United States Patent
Fernald et al.

(10) Patent No.: US 9,810,665 B2
(45) Date of Patent: Nov. 7, 2017

(54) SONIC FILTER FOR MEASURING AND CAPTURING PARTICLES HAVING A PARTICULAR PARTICLE SIZE IN A FLUID, MIXTURE OR PROCESS FLOW

(75) Inventors: Mark R. Fernald, Enfield, CT (US); Timothy J. Bailey, Longmeadow, MA (US)

(73) Assignee: CiDRA CORPORATE SERVICES, INC., Wallingford, CT (US)

( * ) Notice: Subject to any disclaimer, the term of this patent is extended or adjusted under 35 U.S.C. 154(b) by 911 days.

(21) Appl. No.: 13/983,409

(22) PCT Filed: Feb. 6, 2012

(86) PCT No.: PCT/US2012/023973
§ 371 (c)(1),
(2), (4) Date: Nov. 7, 2013

(87) PCT Pub. No.: WO2012/154238
PCT Pub. Date: Nov. 15, 2012

(65) Prior Publication Data
US 2014/0047909 A1  Feb. 20, 2014

Related U.S. Application Data

(60) Provisional application No. 61/439,557, filed on Feb. 4, 2011.

(51) Int. Cl.
*G01N 29/036* (2006.01)
*B01D 21/28* (2006.01)
(Continued)

(52) U.S. Cl.
CPC ......... *G01N 29/036* (2013.01); *B01D 21/283* (2013.01); *B01D 21/34* (2013.01); *H04R 23/00* (2013.01); *G01N 2015/142* (2013.01)

(58) Field of Classification Search
CPC .......... G01N 2015/142; G01N 29/036; B01D 21/283; B01D 21/34; H04R 23/00
See application file for complete search history.

(56) References Cited

U.S. PATENT DOCUMENTS 4,475,921 A * 10/1984 Barmatz ................ B01D 51/08
181/0.5
4,743,361 A   5/1988 Schram
(Continued)

OTHER PUBLICATIONS

Haake, Micromanipulation of Small Particles with Ultrasound. Dissertation [online]. Dec. 1-20, 2004 (Dec. 2004) [retrieved on Jun. 5, 2012 (Jun. 5, 2012)]. Retrieved from the Internet:<URL: http://e-collection.ibrary.ethz.chleserv/eth:27487/eth-27487-02.pdf>.

*Primary Examiner* — John Fitzgerald
(74) *Attorney, Agent, or Firm* — Ware, Fressola, Maguire & Barber LLP

(57) ABSTRACT

Apparatus is provided featuring an acoustic driver and a transducer. The acoustic driver is configured to provide an acoustic driver signal having a frequency that can be adjusted to yield a given wavelength, which in turn, will selectively capture a particular particle size of particles in a fluid, mixture or process flow. The transducer is configured to respond to the acoustic driver signal and provide an acoustic signal having a standing wave at the frequency in order to yield the given wavelength that will selectively capture the particular particle size of the particles in the fluid, mixture or process flow, in order to determine the mass of the particles having the particular particle size in the fluid, mixture or process flow.

19 Claims, 3 Drawing Sheets

(51) Int. Cl.
   *B01D 21/34*   (2006.01)
   *H04R 23/00*   (2006.01)
   G01N 15/14    (2006.01)

(56) References Cited

U.S. PATENT DOCUMENTS

| | | | |
|---|---|---|---|
| 5,245,290 | A | 9/1993 | Cannon et al. |
| 5,769,913 | A * | 6/1998 | Gallego Juarez ...... B01D 51/08 95/29 |
| 6,749,666 | B2 * | 6/2004 | Meegan, Jr. ........... B01D 51/08 55/318 |
| 7,134,320 | B2 | 11/2006 | Gysling et al. |
| 7,150,779 | B2 * | 12/2006 | Meegan, Jr. ........... B01D 51/08 55/318 |
| 7,165,464 | B2 | 1/2007 | Gysling et al. |
| 7,343,820 | B2 | 3/2008 | Gysling et al. |
| 7,363,800 | B2 | 4/2008 | Gysling et al. |
| 7,367,240 | B2 | 5/2008 | Gysling et al. |
| 7,712,381 | B2 * | 5/2010 | Allenberg ............... G01F 1/662 73/861.08 |
| 7,739,869 | B2 * | 6/2010 | Khair ..................... F01N 3/021 60/274 |
| 9,012,830 | B2 * | 4/2015 | Zhu .................... G01N 21/7746 250/227.14 |
| 2004/0065599 | A1 * | 4/2004 | Lal ............................ B01J 8/16 209/659 |
| 2008/0029334 | A1 | 2/2008 | Roach et al. |
| 2009/0158823 | A1 | 6/2009 | Kaduchak et al. |
| 2012/0268731 | A1 * | 10/2012 | Zhu .................... G01N 21/7746 356/73 |

* cited by examiner

SONIC FILTER FOR MEASURING AND CAPTURING PARTICLES HAVING A PARTICULAR PARTICLE SIZE IN A FLUID, MIXTURE OR PROCESS FLOW

CROSS-REFERENCE TO RELATED APPLICATIONS

This application corresponds international patent application serial no. PCT/PCT/US2012/023973, filed 6 Feb. 2012, which claims benefit to provisional patent application Ser. No. 61/439,557, filed 4 Feb. 2011, which is incorporated by reference in its entirety.

BACKGROUND OF THE INVENTION

1. Field of Invention

The present invention relates to techniques for measuring a particular particle size in a fluid, mixture or process flow; and more particularly relates to techniques for measuring and capturing particles having such a particular particle size in such a fluid, mixture or process flow.

2. Description of Related Art

In applications known in the art, there is a need to measure, capture and/or determine a particle size of particles in a fluid, mixture or process flow. Techniques for measuring, capturing and/or determining the particle size of particles in a fluid, mixture or process flow are known in the art, and may include, e.g., techniques based on, or related to, sieve analysis, photoanalysis, optical counting, electro-resistance counting, sedimentation, laser diffraction, acoustic or ultrasound attenuation spectroscopy.

Acoustic standing wave agglomeration technology is known in the art and has been used to filter contaminants from fluids. With this method, contaminants collect in the antinodes of the acoustic field. However, this acoustic standing wave agglomeration technology has not been applied to selectively measure the particular particle size of particles in a fluid, mixture or process flow.

SUMMARY OF THE INVENTION

This invention proposed using acoustic standing wave agglomeration technology to selectively measure the particle size of particles in a fluid, mixture or process flow.

The agglomeration of particles is dependent upon a number of physical properties of the system, such as density of the particle, kinematic viscosity, particle size and wavelength of the standing wave. The wavelength of a standing wave is determined by the drive frequency of the acoustic signal. This frequency can be adjusted to yield a given wavelength which in turn, will selectively capture a particular particle size. The relationship between frequency and particle size are shown below:

$$F_d = (0.48\upsilon)/R^2,$$

where $F_d$=an acoustic drive frequency, and R=a particle radius.

In operation, particle size can be determined by fixing the frequency of the drive acoustics, capturing the associated particles, and then removing the acoustic power. Upon removal of the power, the captured particles will drop due to gravitational forces where the mass can be weighed. Next, the frequency is changed to capture a different particle size, and the process is repeated.

According to some embodiments, the present invention may take the form of an apparatus featuring an acoustic driver and a transducer. The acoustic driver may be configured to provide an acoustic driver signal having a frequency that can be adjusted to yield a given wavelength, which in turn, will selectively capture a particular particle size of particles in a fluid, mixture or process flow. The transducer may be configured to respond to the acoustic driver signal and provide an acoustic signal having a standing wave at the frequency in order to yield the given wavelength that will selectively capture the particle size of the particles in the fluid, mixture or process flow, in order to determine the mass of the particles having the particular particle size in the fluid, mixture or process flow.

According to some embodiments of the present invention, the apparatus may also comprise a particle weighing device configured to determine the mass of the particles having the particular particle size in the fluid, mixture or process flow including by weighing the particles.

According to some embodiments, the present invention may take the form of a method comprising steps of providing with an acoustic driver an acoustic driver signal having a frequency that can be adjusted to yield a given wavelength, which in turn, will selectively capture a particular particle size of particles in a fluid, mixture or process flow; and responding with a transducer to the acoustic driver signal, and providing an acoustic signal having a standing wave at the frequency in order to yield the given wavelength that will selectively capture the particle size of the particles in the fluid, mixture or process flow, in order to determine the mass of the particles having the particular particle size in the fluid, mixture or process flow.

According to some embodiments of the present invention, the method may also comprise determining with a particle weighing device the mass of the particles having the particular particle size in the fluid, mixture or process flow, including by weighing the particles.

The apparatus may take the form of, or the method may be implemented in or by, a sonic filter having some combination of the aforementioned features.

BRIEF DESCRIPTION OF THE DRAWING

The drawing includes FIGS. 1-3, which are not necessarily drawn to scale, as follows.

DETAILED DESCRIPTION OF BEST MODE OF THE INVENTION

Figure 1:
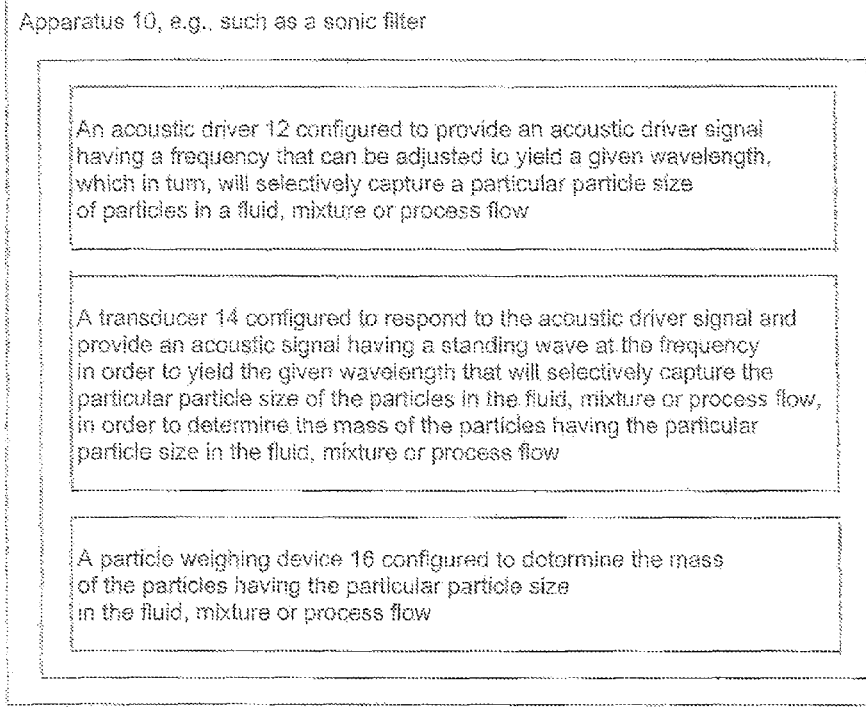
FIG. 1 is a block diagram showing apparatus according to some embodiments of the present invention.
Figure 2:
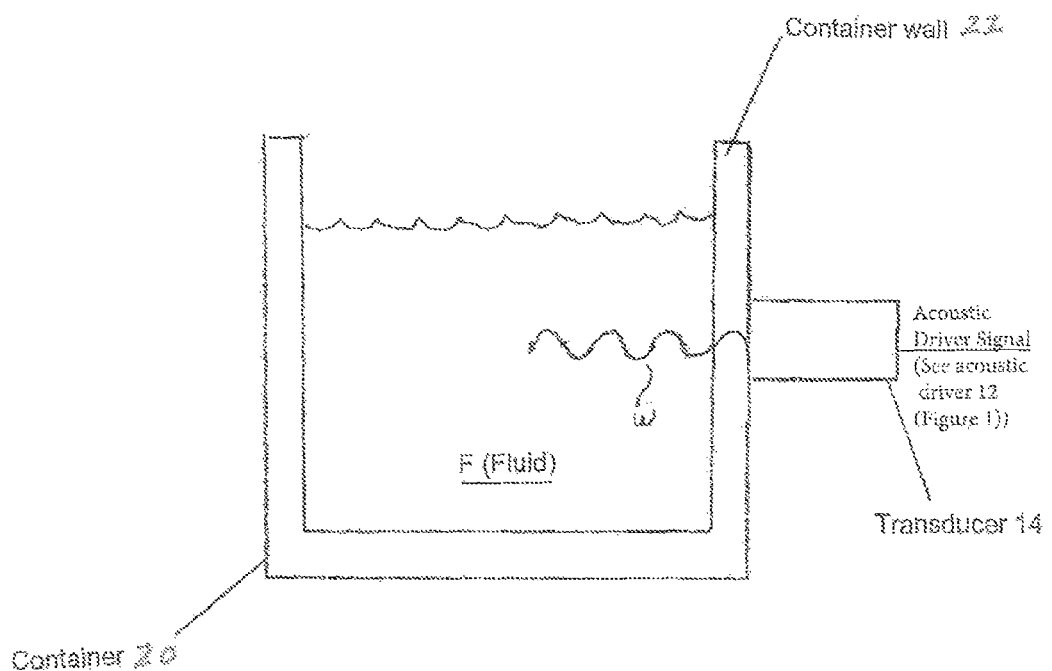
FIG. 2 is a block diagram showing an arrangement of a container and transducer coupled thereto according to some embodiments of the present invention.
Figure 3:
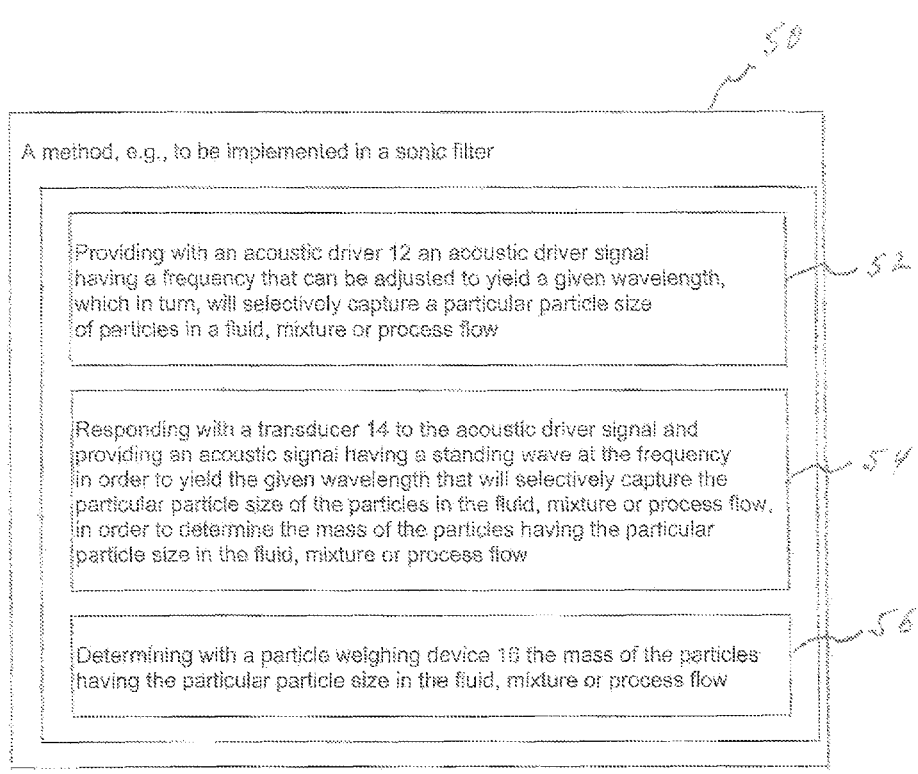
FIG. 3 is a diagram showing a method according to some embodiments of the present invention.

By way of example, FIG. 1 shows the present invention in the form of apparatus generally indicated as 10 featuring an acoustic driver 12 and a transducer 14. According to some embodiments of the present invention, the acoustic driver 12 may be configured to provide an acoustic driver signal having a frequency that can be adjusted to yield a given wavelength, which in turn, will selectively capture a particular particle size of particles in a fluid, mixture or process flow F (FIG. 2). Acoustic drivers like element 12 are known in the art, and the scope of the invention is not intended to be limited to any particular type or kind thereof either now known or later developed in the future. According to some embodiments of the present invention, the transducer 14 may be configured to respond to the acoustic driver signal and provide an acoustic signal having a standing wave W (FIG. 2) at the frequency in order to yield the given wavelength that will selectively capture the particular particle size of the particles in the fluid, mixture or process flow, in order to determine the mass of the particles having the particular particle size in the fluid, mixture or process flow F. The transducer 12 may be configured in a container 20 as shown in FIG. 2, where it is arranged or coupled on the outside wall 22 of the container 20. Transducers like element 14 are known in the art, and the scope of the invention is not intended to be limited to any particular type or kind thereof either now known or later developed in the future.

According to some embodiments of the present invention, the apparatus 10 may be, or form part of, a sonic filter or separator.

According to some embodiments of the present invention, the acoustic driver 12 may be configured to determine the relationship between frequency and the particular particle size using the equation:

$$F_d = (0.48\upsilon)/R^2,$$

where $F_d$=acoustic drive frequency, and R=particle radius. The scope of the invention is not intended to be limited to how the determination of this relationship is made by the acoustic driver 12, e.g., using techniques either now known or later developed in the future. Embodiments are also envisioned where the determination of this relationship is made by another device and provided as an input to the acoustic driver 12.

According to some embodiments of the present invention, the selective capture of the particular particle size of the particles in the fluid, mixture or process flow is based at least partly on an agglomeration of the particles caused by the standing wave. The agglomeration of the particles may be based at least partly on the action or process of collecting the particles in a mass, including by using acoustic energy to vibrate the particles to bring them close together to one another so they stick together. The agglomeration of the particles may be dependent upon a number of physical properties of the system, such as the density of the particles, kinematic viscosity, particle size and wavelength of the standing wave.

According to some embodiments of the present invention, the particle size can be determined by a method or process that includes fixing the frequency of the acoustic drive signal, capturing the associated particles, and then removing the acoustic power. Upon removal of the acoustic power, captured particles will drop due to gravitational forces where the mass of the captured particles can be weighed and measured for the particles having the particular particle size in the fluid, mixture or process flow. The acoustic driver 12 may also be configured to provide the acoustic driver signal having a different frequency that is changed to capture a different particle size, and to repeat the method or process.

According to some embodiments of the present invention, the apparatus 10 may also include a particle weighing device 16 configured to determine the mass of the particles having the particular particle size in the fluid, mixture or process flow F, including by weighing the particles. Particle weighing devices like element 16 are known in the art, and the scope of the invention is not intended to be limited to any particular type or kind thereof either now known or later developed in the future. The scope of the invention is also intended to include other ways to determine the mass of the particles having the particular particle size in the fluid, mixture or process flow F either now known or later developed in the future. The scope of the invention is not intended to be limited to the manner or way in which the particles having the particular particle size are provided to, or received by, the particle weighing device 16.

In FIG. 2, the container 20 having the fluid, mixture or process flow F is shown by way of example. Embodiments are envisioned in which the container 20 may include, or take the form of, a flotation tank, a column, a drum, a tube, a vat, etc. The scope of the invention is also intended to include other types or kinds processing devices or equipment for containing the fluid, mixture or process flow F, e.g., including a process flow pipe.

The Method 50

According to some embodiments, the present invention may take the form of a method generally indicated as 50 having a step 52 for providing with the acoustic driver 12 an acoustic driver signal having the frequency that can be adjusted to yield the given wavelength, which in turn, will selectively capture the particular particle size of the particles in the fluid, mixture or process flow; and also having a step 54 for responding with the transducer 14 to the acoustic driver signal, and providing an acoustic signal having a standing wave at the frequency in order to yield the given wavelength that will selectively capture the particular particle size of the particles in the fluid, mixture or process flow, in order to determine the mass of the particles having the particular particle size in the fluid, mixture or process flow.

Signal Processing

By way of example, and consistent with that described herein, the functionality of the signal processing in the acoustic driver 12, the transducer 14 and/or the particle weighing device 16 may include a signal processing device or signal processor that may be implemented to receive a signal, or provide a signal, or process signals therein, using hardware, software, firmware, or a combination thereof, although the scope of the invention is not intended to be limited to any particular embodiment thereof. In a typical software implementation, the signal processor would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality set forth herein, as well as other functionality described herein without undue experimentation. The scope of the invention is not intended to be limited to any particular implementation using technology now known or later developed in the future. Moreover, the scope of the invention is intended to include a signal processor as either part of the aforementioned devices, as a stand alone module, or in the combination with other circuitry for implementing another module.

It is also understood that the apparatus 10 may include one or more other modules, components, processing circuits, or circuitry for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Applications Re Other Industrial Processes

By way of example, in known industrial processes sound passing through a fluid, mixture, gas/vapor of a process flow, e.g. in a pipe or container, may be sensed and used to determine parameters related to the fluid, mixture, gas/vapor, including a parameter related to a particular particle size. The sound may be generated by equipment operating in association with the process flow, including sound in the form of a standing wave generated by such an appropriate transducer or other known sound generating device that is coupled or connected, e.g., to the outside of a container wall of a container, a pipe wall of a pipe, a tank wall of a tank, etc., consistent with that disclosed in relation to FIGS. 1-2 herein. See also, e.g., the technology disclosed in PCT patent application serial no. PCT/US/27731, filed 9 Mar. 2011, entitled "Method and apparatus for determining GVF (gas volume fraction) for aerated fluids and liquids in flotation tanks, columns, drums, tubes, vats," which has been assigned to the assignee of the present application, and which is hereby incorporated by reference in its entirety.

Further, the present invention also may be used in, or form part of, or used in conjunction with, SONAR-based entrained air meter and metering technology known in the art taking the form of a SONAR-based meter disclosed, e.g., in whole or in part, e.g., in U.S. Pat. Nos. 7,165,464; 7,134,320; 7,363,800; 7,367,240; and 7,343,820.

Furthermore, the present invention may also be used in, or form part of, or used in conjunction with, industrial processes like a mineral extraction processing system for extracting minerals from ore either now known or later developed in the future, including any mineral process, such as those related to processing substances or compounds that result from inorganic processes of nature and/or that are mined from the ground, as well as including either other extraction processing systems or other industrial processes, where the sorting, or classification, of product by size is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A sonic filter (10) that uses a standing wave agglomeration technique to selectively measure particle sizes of particles forming part of a fluid, mixture or process flow (F) in a container (20), comprising:

an acoustic driver (12) that provides an acoustic driver signal having a frequency adjusted to yield a given wavelength for selectively capturing a particular particle size of particles forming part of a fluid, mixture or process flow (F) in a container (20) having a container wall (22), the acoustic driver signal being based upon a relationship between the frequency and the particular particle size using the equation:

$$F_d = (0.48\upsilon)/R^2,$$

where $F_d$=acoustic drive frequency, $\upsilon$=kinematic viscosity, and R=particle radius; and a transducer (14) arranged on the container wall (22), that responds to the acoustic driver signal and provides an acoustic signal having a standing wave (w) at the frequency to yield the given wavelength and selectively capture the particular particle size of the particles in the fluid, mixture or process flow (F) in the container (20), in order to determine the mass of the particles having the particular particle size forming part of the fluid, mixture or process flow (F) and captured in the container (20).

2. A sonic filter (10) according to claim 1, wherein the wavelength of the standing wave (w) is determined by a drive frequency of the acoustic signal.

3. A sonic filter (10) according to claim 1, wherein the selective capture of the particular particle size of the particles in the fluid, mixture or process flow (F) is based at least partly on an agglomeration of the particles in the fluid, mixture or process flow (F) in the container (20) caused by the standing wave (w).

4. A sonic filter (10) according to claim 3, wherein the agglomeration of the particles is based at least partly on the action or process of collecting the particles in a mass, including by using acoustic energy to vibrate the particles to bring them close together to one another so they stick together.

5. A sonic filter (10) according to claim 3, wherein the agglomeration of the particles is dependent upon a number of physical properties of the system, including the density of the particles, kinematic viscosity, particle size and wavelength of the standing wave (w).

6. A sonic filter (10) according to claim 1, wherein the particle size is determined by a process that includes fixing the frequency of the acoustic drive signal, capturing the associated particles, and then removing the acoustic power.

7. A sonic filter (10) according to claim 6, wherein, upon removal of the acoustic power, captured particles will drop due to gravitational forces where the mass of the captured particles is weighed and measured for the particles having the particular particle size in the fluid, mixture or process flow (F).

8. A sonic filter (10) according to claim 7, wherein the acoustic driver (12) provides the acoustic driver signal having a different frequency that is changed to capture a different particle size, and to repeat the process.

9. A sonic filter (10) according to claim 7, wherein the sonic filter (10) comprises a particle weighing device (16) that determines the mass of the captured particles having the particular particle size in the fluid, mixture or process flow (F), including by weighing the captured particles.

10. A method that uses a standing wave agglomeration technique to selectively measure particle sizes of particles forming part of a fluid, mixture or process flow in a container, comprising:

providing with an acoustic driver an acoustic driver signal having a frequency adjusted to yield a given wavelength, which in turn, will selectively capture a particular particle size of particles forming part of a fluid, mixture or process flow in a container having a container wall, the acoustic driver signal being upon a relationship between the frequency and the particular particle size using the equation:

$$F_d = (0.48\upsilon)/R^2,$$

where $F_d$=acoustic drive frequency, $\upsilon$=kinematic viscosity, and R=particle radius; and responding with a transducer arranged on the container wall to the acoustic driver signal, and providing an acoustic signal having a standing wave at the frequency in order to yield the given wavelength that will selectively capture the particular particle size of the particles in the fluid, mixture or process flow, in order to determine the mass of the particles having the particular particle size in the fluid, mixture or process flow.

11. A method according to claim 10, wherein the method comprises determining the wavelength of the standing wave by a drive frequency of the acoustic signal.

12. A sonic filter according to claim 1, wherein the container further comprises a tank, or tank in the form of, a flotation tank, a column, a drum, a tube, or a vat.

13. A method according to claim 10, wherein the method comprises basing at least partly the selective capture of the particular particle size of the particles in the fluid, mixture or process flow on an agglomeration of the particles in the fluid, mixture or process flow in the container caused by the standing wave.

14. A method according to claim 13, wherein the agglomeration of the particles is based at least partly on the action or process of collecting the particles in a mass, including by using acoustic energy to vibrate the particles to bring them close together to one another so they stick together.

15. A method according to claim 13, wherein the agglomeration of the particles is dependent upon a number of physical properties of the system, including density of the particles, kinematic viscosity, particle size and wavelength of the standing wave.

16. A method according to claim 10, wherein the method comprises determining the particle size by a process that includes fixing the frequency of the acoustic drive signal, capturing the associated particles, and then removing the acoustic power.

17. A method according to claim 16, wherein, upon removal of the acoustic power, captured particles will drop due to gravitational forces where the mass of the captured particles is weighed and measured for the captured particles having the particular particle size in the fluid, mixture or process flow.

18. A method according to claim 17, wherein the method comprises providing with the acoustic driver the acoustic driver signal having a different frequency that is changed to capture a different particle size, and repeating the process.

19. A method according to claim 17, wherein the method comprises determining the mass of the captured particles having the particular particle size in the fluid, mixture or process flow, including by weighing the captured particles.

* * * * *